United States Patent [19]

Horiba et al.

[11] Patent Number: 4,672,651

[45] Date of Patent: Jun. 9, 1987

[54] METHOD OF AND APPARATUS FOR RECONSTRUCTING SHAPE OF INTERESTED PART OF OBJECT THROUGH IRRADIATION WITH X-RAYS

[75] Inventors: Isao Horiba, Kariya; Akira Iwata, Nagoya; Nobuo Suzumura, Aichi; Hiroshi Matsuo, Toyonaka, all of Japan

[73] Assignee: Hitachi Medical Corporation, Tokyo, Japan

[21] Appl. No.: 834,814

[22] Filed: Feb. 28, 1986

[30] Foreign Application Priority Data

Mar. 28, 1985 [JP] Japan .................................. 60-62048

[51] Int. Cl.[4] ........................................... G01N 23/04
[52] U.S. Cl. ......................................... 378/62; 378/9; 378/22; 378/901; 364/414
[58] Field of Search ...................... 364/414; 378/62, 8, 378/9, 901, 14, 22–57, 210; 358/111

[56] References Cited

U.S. PATENT DOCUMENTS

4,228,505 10/1980 Wagner ................................ 364/414
4,345,158 8/1982 Pfeites et al. ............................ 378/9

Primary Examiner—Craig E. Church
Assistant Examiner—David P. Porta
Attorney, Agent, or Firm—Antonelli, Terry & Wands

[57] ABSTRACT

An object is irradiated with respective cone-beam like X-rays from first and second directions. For each of the first and second directions are produced mask and live images as respective projection images of the object before and after a contrast medium reaches an interested part of the object. Then, subtraction of the mask image from the live image is made in conjunction with each of the first and second directions. The resulting subtraction image assumes a projection image of the distribution of the contrast medium in the interested part taken in the corresponding direction. The respective projection widths of such projection images of the contrast medium distribution are determined to generate an ellipse defined by the projection widths. The shape of this ellipse is corrected in accordance with individual data values in the projection images of the contrast medium, thereby providing a corrected shape accurately resembling the actual shape of the interested part of the object. The corrected shape of the interested part is displayed.

8 Claims, 7 Drawing Figures

METHOD OF AND APPARATUS FOR RECONSTRUCTING SHAPE OF INTERESTED PART OF OBJECT THROUGH IRRADIATION WITH X-RAYS

BACKGROUND OF THE INVENTION

The present invention relates to a method of and an apparatus for reconstructing the shape of an interested part of an object through irradiation thereof with X-rays and on the basis of data representative of a distribution of the X-ray absorption coefficient of the object. In particular, the invention relates to reconstruct an accurate shape of the interested part. In an application where the interested part is moving, the accurate shape of the interested moving part at any given time phase or at successive time phases can be reconstructed.

Prior art examples will now be described.

PRIOR ART EXAMPLE 1

In a conventional computer tomograph, X-rays are directed toward an object to be examined from a multiplicity of directions, and many data acquired as a result of measurements are processed to obtain a tomographic image representing a two-dimensional distribution of the X-ray absorption coefficient of the object being examined. This apparatus requires measurements from a multiplicity of directions in order to obtain one tomographic image. With such an apparatus, it has been able to obtain a time-averaged tomographic image of an interested moving part of the object, but it has been unable to obtain a more accurate momentary tomographic image of the interested moving part. This is because the motion of the interested moving part is quick as compared to the time length of every measurement, and, as a result, information of motion of the interested moving part at various time phases are mixed in the measured data. In an attempt to obviate the above defect encountered with measurement of motion of the interested moving part which is, for example, the heart which repeats its motion at a constant time period, a method has been proposed according to which data measured at the identical time phase of the periodic motion are only used to obtain a tomographic image of the interested moving part at the specific time phase. However, since the shape of the interested moving part at the identical time phase of every period is not necessarily generally the same in a strict sense, the proposed method is defective in that the tomographic image obtained in the manner described above includes inevitably an averaged component. Also, since the data are measured under the condition of apnoea in the case of the heart, there is the restriction that the tomographic image is reconstructed on the basis of data measured in the time length corresponding to ten-odd heart beats at the most. Therefore, extension of the term of the identical time phase to a range of about 50 ms to 100 ms is required so that data obtained as a result of measurement from various directions can provide information enough to reconstruct the tomographic image of the heart. Thus, the resolution in terms of time is about 50 ms to 100 ms, and the tomographic image is an averaged one from this aspect too.

PRIOR ART EXAMPLE 2

M. K. Thomas et al "The dynamic special reconstructor from basic concepts to applications", 4th CT Physical and Technological Symposium, pp. 1–10, 1981 has proposed an apparatus in which 28 X-ray tubes and the same number of image intensifiers and video cameras are disposed in equally circumferentially spaced-apart relation on a circle. In the proposed apparatus, the X-ray tubes, image intensifiers and video cameras are rotated around an object to be examined at speed as high as 15 rotations per second to project X-rays toward the object from a multiplicity of directions and to measure projected images of the object, and many measurement data thus obtained are arithmetically processed to reconstruct a tomographic image having a resolution as high as 100 frames per second in terms of time. Also, J. Haimson "X-ray Source Without Moving Parts for Ultra-high Speed Tomography", IEEE Trans. NS-26, No. 2 (1979) proposed an X-ray computer tomograph in which an electron beam is cylindrically rotated to rotate the position of X-ray generation at a high speed, thereby entirely eliminating any mechanical movement during measurement. These apparatuses also require measurements from a multiplicity of directions in order to obtain one tomographic image. However, in the case of the former apparatus using many X-ray tubes, the expected density resolution of the tomographic image obtained by reconstruction is as low as about 5% due to degradation of the S/N ratio attributable to an undesirable increase in scattered radiation as a result of projection of the X-rays from various directions and also due to the low S/N ratio in the outputs of the image intensifiers. Also, in the case of the latter apparatus of the electron beam rotation type, generation of an electron beam having high output power, control of the electron beam, etc. are problems that must be technically solved. In addition, the costs of manufacture of these apparatus are estimated to be ten or more times as high as those of conventional apparatus, and the performance/cost ratio of each of these apparatus is not so high. Therefore, it will be difficult for those proposed apparatus to come into wide use.

PRIOR ART EXAMPLE 3

Electrokymography and radarkymography utilizing X-rays for the purpose of observing motion of an interested moving part are well known in the art. The electrokymography was reported by G. C. Henny et al "Electrokymograh for recording heart motion utilizing the roentgenoscope", Am. J. Roentgenol, Vol. 54, p 217, 1945. The radarkymography was reported by L. S. Cohen et al "Heart motion video-tracking (radarkymography) in diagnosis of congeital and acquired heart disease", Am. J. Cardiol. Vol. 22, pp. 678–684, 1968. Both the electrokymography and the radarkymography do not include the step of arithmetic processing and are not intended to detect the external shape itself of an interested part. Rather, they are intended to provide a time-serial signal corresponding to motion of the interested part.

PRIOR ART EXAMPLE 4

An apparatus has been put into practical use in which an object to be examined is irradiated with X-rays before injection of a contrast medium thereby obtaining a first image relevant to the quantity of X-rays absorbed by the object after transmission of X-rays through the object, the object is again irradiated with X-rays after injection of the contrast medium thereby obtaining a second image relevant to the quantity of X-rays absorbed by the object after transmission of X-ray through the object, and digital subtraction of the first image from the second image is then carried out to obtain an image relevant to the distribution of the contrast medium. The size of the region into which the contrast medium is injected can be computed on the basis of the contrast-medium distribution image obtained as a result of processing by the apparatus. Also, the total quantity of the injected contrast medium can be computed by summing up all the distributed values of the contrast medium in the specific region. Further, by dividing the computed total quantity of the contrast medium by the concentration of the contrast medium, the volume of the region having the contrast medium injected therein can be computed for diagnosing the internal state of the object. Further, a method has been proposed in which the apparatus described above is used to obtain contrast-medium distribution images of an injected region observed from two directions angularly spaced apart by about 90° from each other, and, the outer peripheral shape of the injected region (or interested part) is approximated into an ellipse on the basis of the images taken from the two directions. This method was reported by Toraichi et al "System for analysis of contrast picture of left ventricle and its applications", Technical & Research Report of Inst. of Electro. and Commun. Eng. of Japan, MBE-29, Vol. 84, No. 73, 1984 and also S. Eiho et al "Image Processing of X-ray Left Venticular Cineangiocardiograms and Displays of Cardiac Functions", Japanese J. of Soc. of Instrument and Control Engineers, Vol. 19, No. 10, pp. 923–936, 1980. According to this method, the shape of an interested part can be determined on the basis of contrast-medium distribution images taken from two directions only. Therefore, the process of measurement can be simplified. However, because of a mere approximation of the shape of the interested part into an ellipse, this method is insufficient when it is desired to determine or examine a fine geometry or structure of the shape of the interested part. Of course, an accurate shape of an interested part when the part is moving, cannot be determined.

SUMMARY OF THE INVENTION

An object of the invention is to provide a method and an apparatus in which an accurate shape of an interested part of an object can be reconstructed through irradiation of the object with X-rays from two different directions and on the basis of contrast-medium distribution images taken from the two directions.

Another object of the invention is to reconstruct an accurate shape of an interested part of an object at any given time phase or at successive time phases when the interested part repeats a motion at a substantially constant period.

According to the present invention, first and second projection images (called mask and live images) of an object before and after a contrast medium reaches an interested part of the object, are produced for each of two different directions from which respective cone-beam like X-rays are directed toward the object. The projection image of the object represents a group of data values indicative of absorbances through the object for respective beams in the cone-beam like X-rays in the associated direction. Then, subtraction of the mask image from the live image for each of the two directions is made. The resulting subtraction image assumes a projection image of the distribution of the contrast medium in the interested part of the object taken in the corresponding direction. The respective widths of projection of the two projection images of the contrast medium distribution are determined to establish an ellipse defined by the projection widths. This ellipse represents a rough shape of the interested part of the object. The shape of this ellipse is modified or corrected in accordance with individual data values in the projection images of the contrast medium distribution for the two directions, thereby producing a corrected shape which accurately resembles the actual shape of the interested part of the object.

When the interested part of the object repeats a motion at a substantially constant period, the present invention may include deriving from the object a monitor signal which resembles the motion of the interested part. The derived monitor signal is used to obtain projection images of the contrast medium distribution taken for two directions at the substantially identical time phases of the periodical motion of the interested part. Thus, an accurate shape of the moving interested part at any given time phase or at successive time phases can be reconstructed.

DESCRIPTION OF THE PREFERRED EMBODIMENTS

Figure 1:
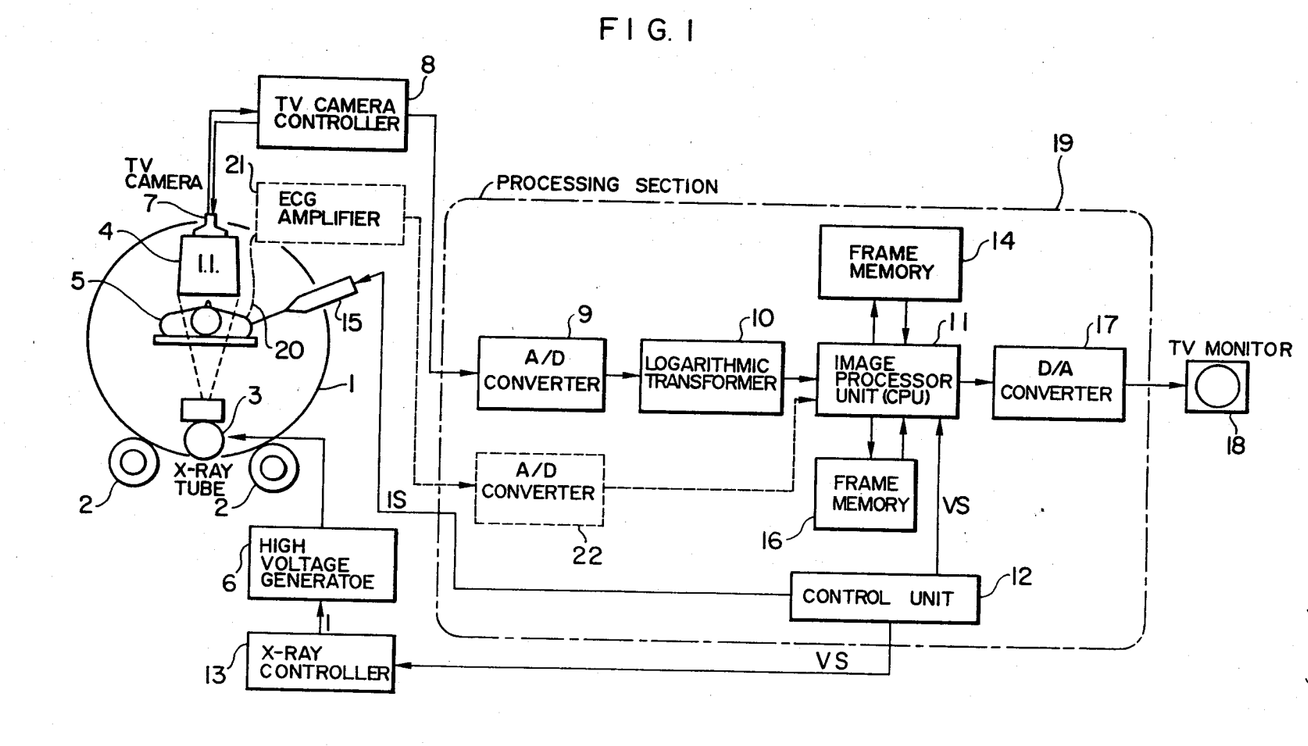
FIG. 1 is a systematic diagram showing the structure of a preferred embodiment of an apparatus according to the present invention.

The structure of a preferred embodiment of an apparatus according to the present invention is diagrammatically shown in FIG. 1.

Figure 2:
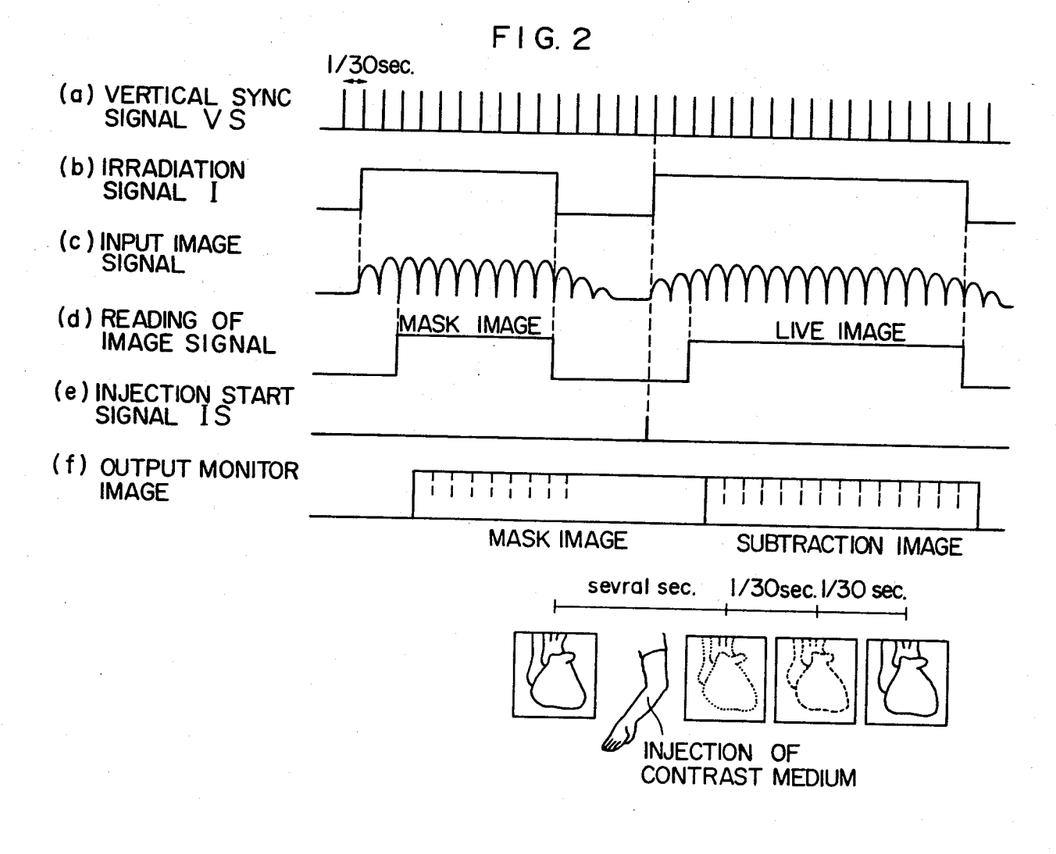
FIG. 2 is a time chart showing a time sequence of measurement in the present invention.

Referring to FIG. 1, a supporting frame 1 is rotated by rollers 2. An X-ray source 3 is disposed opposite to an X-ray detector 4 with an object 5 (to be examined) interposed therebetween and is supported together with the X-ray detector 4 on the supporting frame 1. The X-ray source 3 generates cone-beam like X-rays in the form of a cone upon application of a high voltage from a high voltage generator 6 thereto. The X-ray detector 4, which is an image intensifier, detects X-rays transmitted through the object 5. The detector 4 also functions to electron-multiply the detected X-rays for conversion into an optical image. It is preferable that the size of an X-ray detecting surface of the X-ray detector 4 can cover that part of the X-rays which are transmitted through at least an interested part of the object 5. A TV camera 7 is coupled to the X-ray detector 4 through an optical lens (not shown) to convert the optical image into an electrical signal. The TV camera 7 is controlled in a well known manner by a TV camera controller 8 which in turn amplifies suitably the electrical output signal of the TV camera 7. The amplified signal is converted into a digital value by an A/D converter 9, and a logarithmic transformer 10 transforms the digital output of the A/D converter 9 into a logarithmic value which represents X-ray absorbance of the object 5. The logarithmic output of the logarithmic transformer 10 is applied to an image processor unit 11. Alternatively, the A/D conversion may be carried out after the logarithmic conversion. The above manner of measurement is done in a specific position where the supporting frame 1 is fixed relative to the object 5. FIG. 2 illustrates a time chart of measurement.

A vertical sync signal VS shown in (a) of FIG. 2 is generated from a control unit 12. The vertical sync signal VS is applied to an X-ray controller 13. The X-ray controller 13 supplies an X-ray irradiation signal I, as shown in (b) of FIG. 2, to the high voltage generator 6 so that the object 5 is irradiated with X-rays at timing shown in FIG. 2. The vertical sync signal VS from the control unit 12 is also applied at the same time to the image processor unit 11. In an input image signal as shown in (c) of FIG. 2, appearing from the logarithmic transformer 10, a portion after stabilization of the electrical output signal from the TV camera 7 is read by the image processor unit 11 in synchronism with the vertical sync signal VS, as shown in (d) of FIG. 2. A contrast medium is used in the series of measurement. An image obtained before injection of the contrast medium into the object 5 is called a mask image, and that obtained after injection of the contrast medium is called a line image. In the case of the time chart shown in FIG. 2, the mask image is measured eight times. These eight mask images are successively converted into television image signals again by a D/A converter 17 to be displayed on a TV monitor 18. At the same time, these eight mask images are summed and averaged in the image processor unit 11, and the averaged image is stored in a first frame memory 14. This summing and averaging processing is effective for reducing noises that may be included in the images. After the measurement of the mask images, a contrast-medium injection start signal IS as shown in (e) of FIG. 2 is applied from the control unit 12 to a contrast medium injector 15 in synchronism with the vertical sync signal VS. The contrast medium is injected into the object 5, and, at the same time, the X-ray irradiation signal I is applied to the high voltage generator 6 again to start measurement of live images. Though the contrast-medium injection start signal IS is shown at the timing after the measurement of the mask images for the purpose of simplicity of illustration, the timing of the signal IS may be arbitrary so long as the mask images are measured before arrival of the contrast medium to the interested object part while the live images are measured after arrival of the contrast medium. In the image processor unit 11, the mask image stored already in the first frame memory 14 is subtracted from each of the live images. The resultant subtraction images are successively stored in a second frame memory 16, and, at the same time, converted by the D/A converter 17 into television image signals again to be applied to the TV monitor 18. Thus, the state of the contrast medium changing every moment in the object 5 is displayed in real time as a moving image on the TV monitor 18, as shown in (f) of FIG. 2.

A subtraction image $D_i(x, y)$ stored in the second frame memory 16 will be described in more detail. When the distribution of the X-ray absorption coefficient of the object 5 before injection of the contrast medium is expressed as $\mu$ (u, v, w), a mask image $M_i(x, y)$ is given by $$M_i(x, y) = \int \mu (u, v, w) dZ_i \qquad (1)$$

where $Z_i$ is the direction of irradiation with the X-rays. Then, when the contrast medium distribution after injection of the contrast medium into the object 5 is expressed as C (u, v, w), a live image $L_i(x, y)$ is given by $$L_i(x, y) = \int \{\mu (u, v, w) + C(u, v, w)\} dZ_i \qquad (2)$$

Therefore, the subtraction image $D_i(x, y)$ is given by $$D_i(x, y) = L_i(x, y) - M_i(x, y) \qquad (3)$$

$$D_i(x, y) = \int C(u, v, w) dZ_i \qquad (4)$$

Thus, an integrated image or a projection image representing the result of integration of the distribution of the contrast medium in the object 5 in the direction $Z_i$ is obtained. Each of the mask image $M_i(x, y)$ and the live image $L_i(x, y)$ represents a projection image of the object 5 or a group of data values indicative of absorbances through the object 5 for respective beams in the cone-beam like X-rays in the direction $Z_i$.

In the manner above described, a series of projection images of the contrast medium in the object 5 are measured for the cone-beam like X-rays from a first direction, i.e. at the first position where the supporting frame 1 is fixed relative to the object 5. Then, the supporting frame 1 is rotated to and fixed at a second position angularly spaced apart by about 90° from the first position, and a series of projection images $D_j(x, y)$ of the contrast medium in the object 5 are measured for the cone-beam like X-rays from a second direction in a manner similar to that described above. This projection image $D_j(x, y)$ is given by the following equation (5) corresponding to the equation (4):

$$D_j(x, y) = \int C(u, v, w) dZ_j \qquad (5)$$

Thus, each of the subtraction images $D_i(x, y)$ and $D_j(x, y)$ is a projection image representative of the internal contrast-medium distribution of the object in the direction of the measurement (that is, an integrated image of the contrast-medium absorption coefficient in the X-ray beam direction the cone-beam like X-rays).

Figure 3:
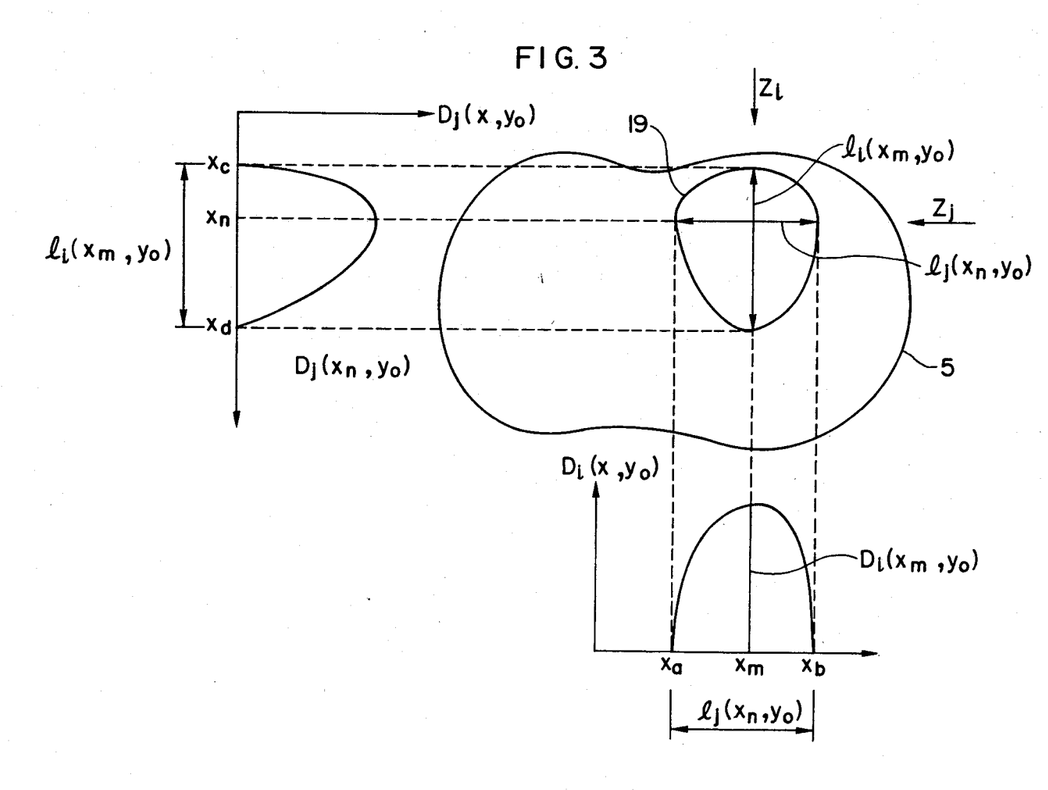
FIG. 3 illustrates how a true-length projection chart of an interested part is obtained on the basis of projection images.

Herein, the live images $L_i$ and $L_j$ are those obtained when the contrast medium is directly injected into an interested part of the object 5 and is sufficiently filled therein or when the contrast medium injected from an injecting part is uniformly filled in an interested part after flowing through a diffusion region. When the live images $L_i$ and $L_j$ are such as those specified above, the corresponding subtraction images $D_i(x, y)$ and $D_j(x, y)$ are expressed as $$D_i(x, y) = C_i \cdot l_i(x, y) \qquad (6)$$

$$D_j(x, y) = C_j \cdot l_j(x, y) \qquad (7)$$

where $C_i$ and $C_j$ are the contrast-medium absorption coefficients of the interested part respectively, and $l_i$ and $l_j$ are the lengths of the interested part in the directions $Z_i$ and $Z_j$ respectively. FIG. 3 shows the correlation of $D_i$, $D_j$, $l_i$ and $l_j$.

FIG. 3 is a sectional view of a three-dimensional object 5 taken on a section where y=yo. An interested part 19 exists inside the object 5 in FIG. 3. Herein, the interested part 19 is a cavity which is connected by a blood vessel to a contrast-medium injecting portion at a position not shown in FIG. 3. A projection image $D_i(x, y_o)$ in the direction $Z_i$ is related to the product of the concentration $C_i$ of the contrast medium injected for measurement of a live image in the direction $Z_i$ and the length $l_i(x, y_o)$. There is also a similar relation in the case of a projection image $D_j(x, y_o)$ in the direction $Z_j$.

In the case where the concentrations $C_i$ and $C_j$ of the contrast medium are known already, the lengths $l_i(x, y)$ and $l_j(x, y)$ can be readily determined according to the equations (6) and (7) respectively.

On the other hand, in the case where the contrast-medium concentrations $C_i$ and $C_j$ are unknown, the values of $C_i$ and $C_j$ can be computed when the shape of the interested part is analogous substantially to a convex form similar to an ellipsoid. That is, when the shape of the interested part filled with the contrast medium is analogous to an ellipse in section, the distance between the rising position $x_a$ of the projection image in the direction $Z_i$ and the opposite rising position (falling position) $x_b$ corresponds to the maximum width of the interested part in the direction $Z_j$. Similarly, the distance between the positions $x_c$ and $x_d$ of the projection image $D_j$ in the direction $Z_j$ corresponds to the maximum width of the interested part in the direction $Z_i$. These maximum widths in the directions $Z_i$ and $Z_j$ are directly reflected in the projection images, when the absorption coefficient of the interested part is uniform, and correspond to the positions providing the maximum values of the projection images $D_i$ and $D_j$. Therefore, for the computation of the concentration $C_i$, the length $l_i(x_m, y_o)$ is first determined on the basis of the difference between the rising positions $x_c$ and $x_d$ of the projection image $D_j(x, y_o)$, as follows:

$$l_i(x_m, y_o) = |x_d - x_c| \qquad (8)$$

Then, the maximum value $D_i(x_m, y_o)$ of the projection image $D_i(x, y)$ is used to determine the value of $C_i$ as follows:

$$C_i = D_i(x_m, y_o)/l_i(x_m, y_o) \qquad (9)$$

Similarly, for the computation of the concentration $C_j$, the length $l_j(x_n, y_o)$ is first determined on the basis of the difference between the rising positions $x_a$ and $x_b$ of the projection image $D_i(x, y_o)$, as follows:

$$l_j(x_n, y_o) = |x_b - x_a| \qquad (10)$$

Then, the maximum value $D_j(x_n, y_o)$ of the projection image $D_j(x, y_o)$ is used to determine the value of $C_j$ as follows:

$$C_j = D_j(x_n, y_o)/l_j(x_n, y_o) \qquad (11)$$

Thus, even in the case where the coefficient of absorption of the contrast medium used for measurement is unknown, the concentrations $C_i$ and $C_j$ can be determined according to the equations (8) to (10) when the noted portion filled with the contrast medium has a shape analogous to an ellipse in section. FIG. 3 illustrates the section taken at $y = y_o$. It is apparent that, in the case of other sections taken at $y \neq y_o$, too, the lengths $l_i$ and $l_j$ can be entirely similarly determined from the projection images $D_i$ and $D_j$ by determining the values of $C_i$ and $C_j$.

How to compute the shape F of the interested part on the basis of the values of $l_i$ and $l_j$ will be now described. For a ready understanding of the method, computation of the shape F on the section taken at $y = y_o$ will be described by way of example. The shape F of the interested part is determined by repeating relaxative corrections or modifications in the directions $Z_i$ and $Z_j$ until the length of F in the direction $Z_i$ becomes equal to the length $l_i$ at each of individual positions of x, and, also, the length of F in the direction $Z_j$ becomes equal to the length $l_j$ at each of individual positions of x.

It is supposed that the shape F to be corrected or modified is an ellipse $F_o$ whose major and minor axes are defined by the maximum length $l_i(x_m, y_o)$ in the direction $Z_i$ and the maximum length $l_j(x_n, y_o)$ in the direction $Z_j$. Herein, the larger one of $l_i$ and $l_j$ provides the major axis, and the smaller one of $l_i$ and $l_j$ provides the minor axis. The relaxative correction procedure starting from such an initial image $F_o$ is similar to that disclosed in JP-A No. 58-136334 laid open on Aug. 13, 1983.

Figure 4:
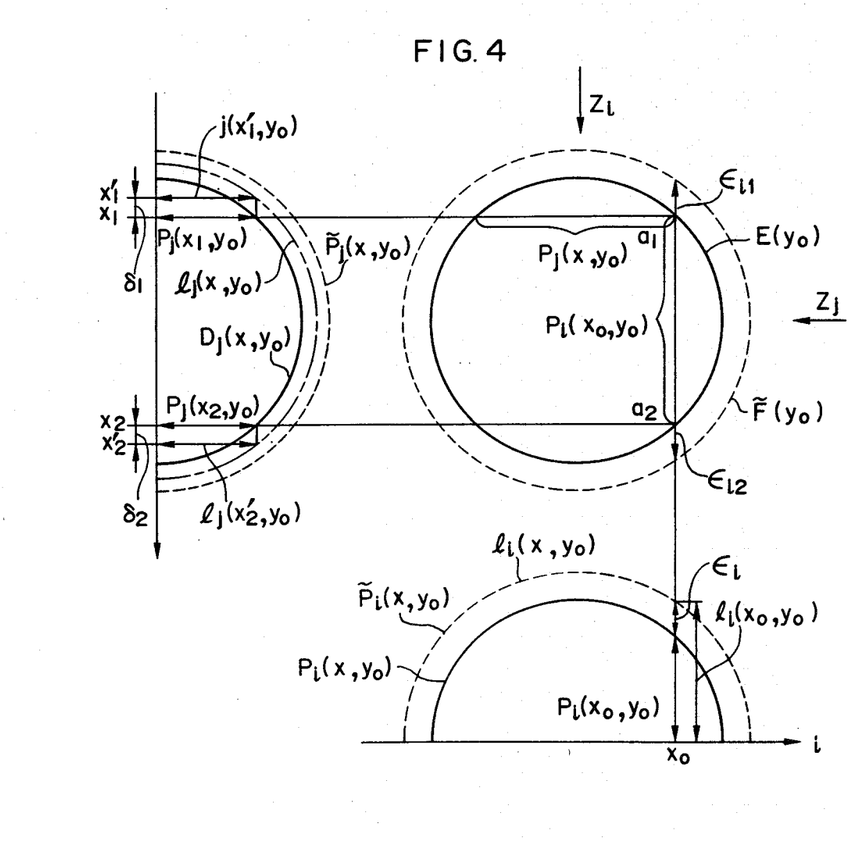
FIG. 4 illustrates how the shape of the interested part of an object is determined by a relaxative correction procedure.

FIG. 4 illustrates the manner of computation.

In FIG. 4, $P_i(x, y_o)$ and $P_j(x, y_o)$ designate the thicknesses in the directions $Z_i$ and $Z_j$ respectively when computed on the basis of the initial shape F to be corrected. The difference $\epsilon_i$ between the $Z_i$-direction length $l_i(x, y_o)$ determined from the measured subtraction image $D_i(x, y_o)$ and the thickness $P_i(x, y_o)$ is computed according to the following equation (12), and error correction factors $\epsilon_{i1}$ and $\epsilon_{i2}$ are computed according to the following equations (13) and (14) respectively, thereby correcting the shape F to obtain a corrected shape $\widetilde{F}$:

$$\epsilon_i = l_i(x, y_o) - P_i(x, y_o) \qquad (12)$$

$$\epsilon_{i1} = \frac{\delta_1}{\delta_1 + \delta_2} \epsilon_i \qquad (13)$$

$$\delta_{i2} = \frac{\delta_2}{\delta_1 + \delta_2} \epsilon_i \qquad (14)$$

Factors $\delta_1$ and $\delta_2$ in the equations (13) and (14) are determined as follows. When it is desired to correct the shape F on the basis of the difference between $P_i(x, y_o)$ and $l_i(x, y_o)$ at a detecting position x, that is, the error $\epsilon_i$, a detecting position $x_1'$ (or $x_2'$) is found where $P_j(x_1, y_o)$ (or $P_j(x_2, y_o)$) representative of the thickness of the shape F along the X-ray beam coming from the direction $Z_j$ and passing through the intersection $a_1$ (or $a_2$) between the shape F and the X-ray beam coming from the direction $Z_i$ and passing through the point $x_o$ becomes equal to $l_j(x, y_o)$ derived from the data measured in the direction $Z_j$. Then, the factors $\delta_1$ and $\delta_2$ are selected to correspond to the distance between the points $x_1$ and $x_1'$ and the distance between the points $x_2$ and $x_2'$ respectively.

In the manner described above, the shape $\widetilde{F}$ is corrected to the corrected shape on the basis of the length $l_i(x, y_o)$ measured in the direction $Z_i$. However, the $Z_j$-direction length $\widetilde{P}_j(x, y_o)$ obtained from the corrected shape $\widetilde{F}$ is not necessarily equal to $Z_j$-direction length $l_j(x, y_o)$. Therefore, the difference therebetween is evaluated by the following equations:

$$\widetilde{E} = \sum^x [\widetilde{P}_j(x, y_o) - l_j(x, y_o)]^2 \qquad (15)$$

-continued $$E = \sum^{x} [P_j(x, y_o) - l_j(x, y_o)]^2 \quad (16)$$

where $\bar{E}$ represents the error after correction, and E represents the error before correction.

When the degree of error improvement becomes smaller than a certain value, that is, when the relation $$|\bar{E} - E| < \Delta E \quad (17)$$

is satisfied, the corrected shape F satisfying the above relation is taken as a final corrected shape $\bar{F}$ ($y_o$) of the interested part 19, and the procedure for correction is ended. When, on the other hand, the relation (17) is not satisfied, the corrected shape $\bar{F}$ is employed as a shape F to be corrected again, and processing similar to that described above is repeated. In such a case, however, the suffixes i and j in the data processed in the former case are interchanged in the computations. That is, on the basis of the difference between the $Z_j$-direction thickness $P_j$ (x, $y_o$) of the shape F to be corrected and the measured length data $l_j$ (x, $y_o$), the shape F is corrected to obtain a corrected shape $\bar{F}$. In the equations (15) and (16) defining the errors $\bar{E}$ and E, the suffixes i and j are interchanged, and, when the relation (17) is finally satisfied, the corrected shape $\bar{F}$ satisfying the relation (17) is employed as a final corrected shape F ($y_o$) to end the procedure for correction. On the other hand, when the relation (17) is not still satisfied, the corrected shape $\bar{F}$ is employed as a shape F to be corrected again, and, while interchanging the suffixes i and j, processing similar to that described already is repeated.

By sequentially executing the above procedure at each of a series of time t, the shape of the interested part 19 can be configured.

In the above description, the directions $Z_i$ and $Z_j$ are orthogonal to each other. It is apparent, however, that the directions $Z_i$ and $Z_j$ need not necessarily be orthogonal to each other.

The above description has referred to the manner of determination of the shape of an interested part on a section taken at y=$y_o$. It is apparent that the shape of such a part on a section at y≠$y_o$ can also entirely similarly be determined.

By determining the two-dimensional shapes F(y) of the interested part on various sections, the three-dimensional shape of the interested part can be obtained.

Though in FIG. 2 the mask and subtraction images have been displayed on the TV monitor 18 in real time, only the displaying of a corrected shape of the interested part suffices for the purpose of the present invention.

Figure 6:
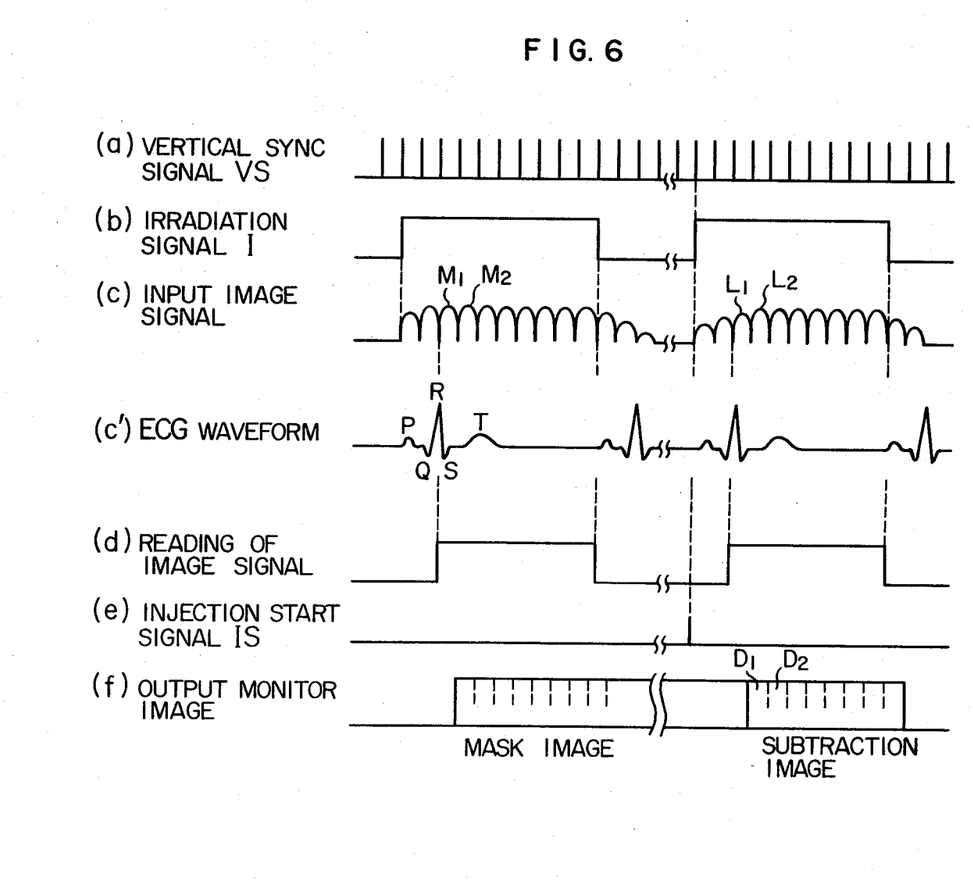
FIG. 6 is a time chart showing a time sequence of measurement when the interested part of an object is moving.

The foregoing description has not referred to determination of the shape of a moving interested part. Though there are many objects which are entirely stationary, there is also an object, such as the heart of a living body, which repeats a rhythmic motion at a generally constant period. To deal with such a moving interested part, the period of the rhythmic motion is detected. The embodiment shown in FIG. 1 utilizes an electrocardiogram for the purpose of detection of the period of rhythmic motion of the heart. FIG. 6 illustrates a time sequence of measurement in such a case. An electrode 20 is attached to the surface of the body of the object 5 to transduce the motion of the heart into an electrical signal (see (c') of FIG. 6). This electrical signal is amplified by an EGG amplifier 21 and, after being converted into a digital signal by an A/D converter 22, applied to the image processor unit 11 together with the X-ray image (mask or live image) signal. The X-ray images and electrocardiograms (ECG's) are similarly measured at positions spaced apart by 90° from each other. The X-ray images relevant to the identical portions of the ECG waveform are used as independent data at individual time phases of the ECG waveform in order to determine the three-dimensional shape of the heart according to the procedure described above.

More detailed explanation will now be made referring to FIG. 6. FIGS. 6(a) to 6(f) correspond to FIGS. 2(a) to 2(f) respectively. Mask images $M_1$, $M_2$, ---and live images $L_1$, $L_2$, --- shown in (c) of FIG. 6 are obtained in a similar manner to the embodiment described in conjunction with FIG. 2. In the present embodiment, subtraction is made for the mask and live images ($M_1$ and $L_1$, $M_2$ and $L_2$ corresponding to the identical time phases of the ECG waveform shown in (c') of FIG. 6 to produce a subtraction image ($D_1$, $D_2$, ---), and such subtraction images in different directions are used to determine and display the shape of an interested part at a special time phase (for example, R-wave) or at successive time phases. Extraction of the mask and live images corresponding to the identical time phases of the ECG waveform can be readily made in such a manner that, in the image processor unit 11, each period of the electrical signal supplied thereto representing the ECG waveform is divided into equal segments and the combination of a mask image and a live image corresponding to the identical time phase segments are selected from the mask images and live images taken in the image processor unit 11. With respect to this kind of technique, one can refer to R. J. Alfide et al "Gated computed tomography of the heart, Computed Axial Tomography 1", pp. 51-57, 1977 and D. F. Adams et al "Determination of myocardial ischemia and perfusion by CCT, CT of the Heart and the Great Vessels: Experimental Evaluation and Clinical Application", edited by C. B. Higgins, pp. 277-287, FUTUBA, 1983.

Figure 5:
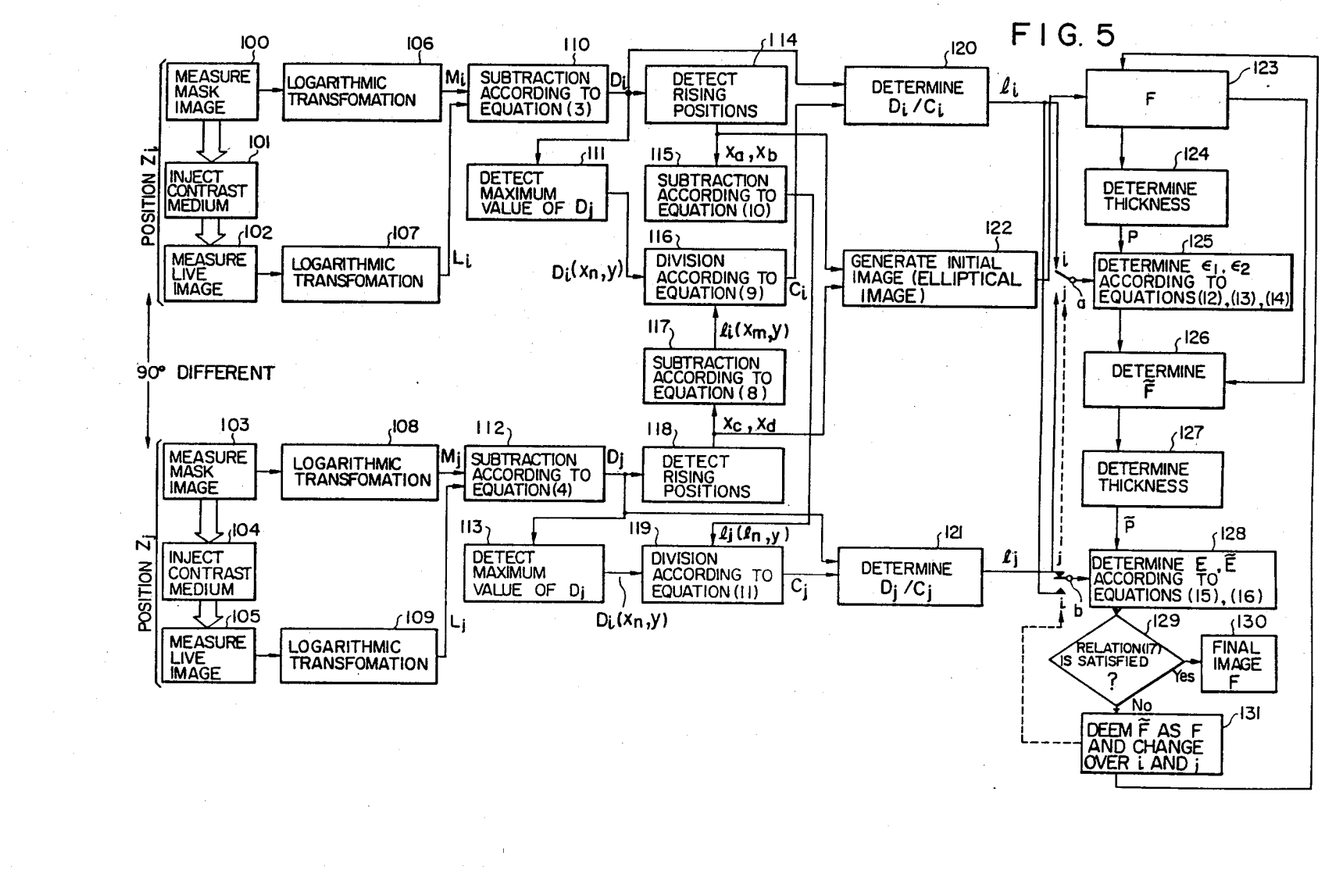
FIG. 5 is an overall flow chart of processing according to the present invention.

FIG. 5 shows an overall flow chart of processing executed in the aforementioned embodiments of the present invention.

In step 100, a mask image of an object to be examined is measured at a position $Z_i$ by the measuring system of the apparatus shown in FIG. 1. Then, in step 101, a contrast medium is injected into the object, and, in step 102, a live image is measured after the contrast medium has been filled in an interested part of the object. In step 103, a mask image is measured at a position $Z_j$ where the X-ray tube 3 and the X-ray detector 4 are rotated through an angle of about 90° relative to the former position $Z_i$. In step 104, the contrast medium is injected, and, in step 105, a live image is similarly measured.

Figure 7:
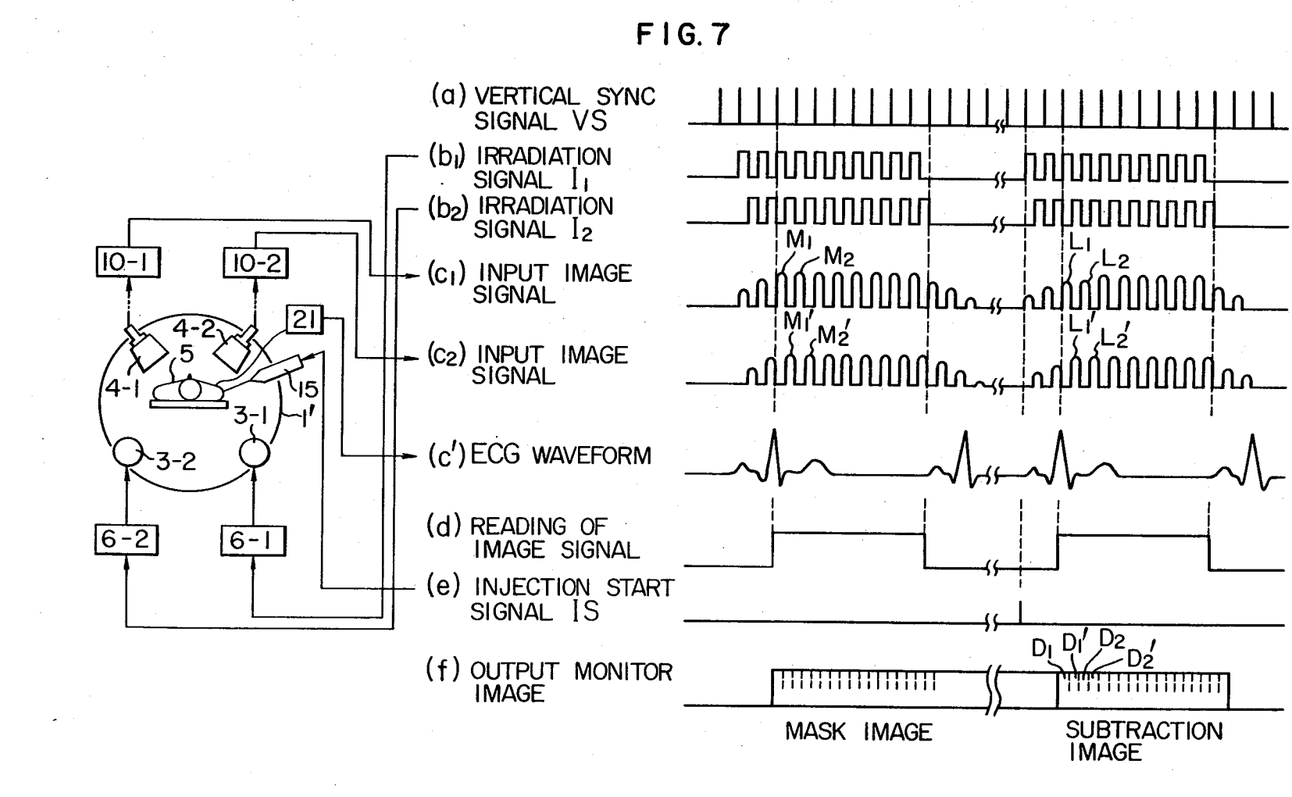
FIG. 7 is a time chart showing a time sequence of measurement in another embodiment of the present invention in which two pairs of X-ray source and X-ray detector are used.

Although the above description has referred to the case where one pair of the X-ray tube 3 and detector 4 is used to make two measurements at two angularly spaced-apart positions respectively, two pairs of X-ray tubes and detectors may be previously disposed at two positions spaced apart by an angle of about 90° respectively. In such a case, the contrast medium need not be injected in each of the steps 101 and 104. For example, the contrast medium may be injected once after substantially simultaneous measurement of the mask images in the two different directions, and the live images may be simultaneously measured in the two directions. A time sequence of measurement in such a case is shown in FIG. 7 together with a measuring system in conjunction with the case where the interested part of an object is moving. A first pair of X-ray source 3-1 and X-ray detector 4-1 and a second pair of X-ray source 3-2 and X-ray detector 4-2 are arranged on a supporting frame 1' in first and second directions different from each other by about 90°, the paired X-ray source and X-ray detector being disposed opposite to each other with the object 5 interposed therebetween. A vertical sync signal VS ((a) of FIG. 7) is applied from the control unit 12 to the X-ray controller 13 which in turn supplies alternate X-ray irradiation signals $I_1$ and $I_2$ (see ($b_1$) and ($b_2$) of FIG. 7) to high voltage generators 6-1 and 6-2 so that cone-beam like X-rays are generated from the X-ray sources 3-1 and 3-2 alternately in the first and second directions. X-rays transmitted through the object 5 are received by the X-ray detectors 4-1 and 4-2 and are transformed by logarithmic transformers 10-1 and 10-2 into X-ray absorption coefficients to provide input image signals (see ($c_1$) and ($c_2$) of FIG. 7) to the image processor unit 11. In this manner, discrete mask images $M_1$, $M_2$, --- are derived from the X-ray detector 4-1 while discrete mask images $M_1'$, $M_2'$ --- are derived from the detector 4-2. The mask images $M_1$ and $M_1'$, $M_2$ and $M_2'$; --- are adjacent to each other such that they can be regarded as being at the substantially same time phase. After the measurement of the mask images, a contrast medium injection signal IS is applied from the control unit 12 to the contrast medium injector 15 and at the same time the X-ray irradiation signals $I_1$ and $I_2$ are applied to the high voltage generators 6-1 and 6-2 again to carry out the measurement of live images. By using an ECG waveform ((c') of FIG. 7), the image processor unit 11 successively produces subtraction images $D_1$, $D_1'$, $D_2$, $D_2'$, --- for the mask and live images $M_1$ and $L_1$, $M_1'$ and $L_1'$, $M_2$ and $L_2$, $M_2'$ and $L_2'$, ---corresponding to the identical time phases of the ECG waveform. Though in the explained example the contrast medium has been injected once, there may be employed a method by which the use of the first pair of X-ray source 3-1 and X-ray detector 4-1 and a first injection of contrast medium are carried out to produce mask images and live images for the first direction and thereafter the use of the second pair of X-ray source 3-2 and X-ray detector 4-2 and a second injection of contrast medium are carried out to produce mask images and live images for the second direction. Since a time sequence of measurement in that case will be apparent to those skilled in the art, further explanation is omitted herein. Also, though FIG. 7 has illustrated the case of the moving interested part, a time sequence of measurement, when two pairs of X-ray sources and X-ray detectors are employed but which corresponds to the case of the stationary interested part in the FIG. 2 embodiment, will be self-evident from FIG. 7 when comparing FIGS. 2 and 6.

Now returning to FIG. 5, in steps 106, 107, 108 and 109, the two sets of the mask images and live images measured by the series of steps 100 to 105 described above are transformed by the logarithmic transformer 10. That is, the mask image and live image measured at the position $Z_i$ are transformed into $M_i(x, y)$ and $L_i(x, y)$ according to the equations (1) and (2) respectively. Similarly, the mask image and live image measured at the position $Z_j$ are transformed into $M_j(x, y)$ and $L_j(x, y)$ respectively. Then, in steps 110 and 112, a subtraction image computing unit in the image processor unit 11 carries out subtraction of the individual mask images from the corresponding live images according to the equations and (4) and (5) respectively, thereby providing projection images $D_i(x, y)$ and $D_j(x, y)$ representing distributions of the contrast medium in the object.

Then, the values of the contrast-medium absorption coefficient are computed. First, in step 114, the rising positions $x_a$ and $x_b$ are detected from the projection image $D_i(x, y)$ representing the distribution of the contrast medium. Although various methods can be used for the detection of the rising positions $x_a$ and $x_b$, the maximum value of the second-order differential of D (x, y) is preferably used in the embodiment of the present invention. The detail of this method is disclosed by Matsuo, Iwata, Horiba, Suzumura and Takahashi "Algorithm suitable for application to digital subtraction angiography for automatically depicting profile of left ventricle", Technical & Research Report of Inst. of Electro. and Commun. Eng. of Japan, MBE 84-50, pp. 31–38, 1984. Therefore, any detailed description of this method is omitted. In step 115, the value of $x_a$ is subtracted from that of $x_b$ according to the equation (10) to produce $l_j(x_o, y)$.

In step 111, the maximum value $D_i(x_m, y)$ of $D_i(x, y)$ is detected. For this purpose, maximum values in the x-direction classified by the value of y are compared to find the desired value. The same applies to the processing of data in the direction $Z_j$. That is, in step 118, the rising positions $x_c$ and $x_d$ are detected from $D_j(x, y)$, and, in step 117, $l_i(x_m, y)$ is computed according to the equation (8). Also, in step 113, $D_j(x_n, y)$ is detected as the maximum value of $D_j(x, y)$. In step 116, the value of $D_i(x_m, y)$ is divided by the value of $l_i(x_m, y)$ according to the equation (9) to compute the contrast-medium absorption coefficient $C_i$. Also, in step 119, the value of $D_j(x_n, y)$ is divided by the value of $l_j(x_n, y)$ according to the equation (11) to compute the contrast-medium absorption coefficient $C_j$.

Then, the computed values of the contrast-medium absorption coefficients $C_i$ and $C_j$ are used to transform the projection images $D_i(x, y)$ and $D_j(x, y)$ into the true lengths. That is, in steps 120 and 121, $D_i(x, y)$ and $D_j(x, y)$ are divided by $C_i$ and $C_j$ to compute the thicknesses $l_i(x, y)$ and $l_j(x, y)$ respectively.

Then, the shape of the interested part is determined by relaxative approximation using the thickness data $l_i(x, y)$ and $l_j(x, y)$ in the two directions $Z_i$ and $Z_j$. First, in step 122, an elliptical image, which is an initial image used for relaxative approximation, is determined on the basis of the values of $x_a$, $x_b$, $x_c$ and $x_d$. This elliptical image is generated on a three-dimensional memory array. When the coordinate system of this three-dimensional memory array is expressed as (i, j, y), the center O ($i_o$, $j_o$, y) of the ellipse dependent upon the position of y is expressed as $$\left. \begin{array}{l} i_o = \dfrac{x_a + x_b}{2} \\ j_o = \dfrac{x_c + x_d}{2} \end{array} \right\} \quad (18)$$

The lengths of the major axis and minor axis of the ellipse are $l_i(x_m, y)$ and $l_j(x_n, y)$ respectively. When all the values inside this ellipse are designated as "1", and those outside the ellipse are designated as "0", the thickness in the directions $Z_i$ and $Z_j$ can be simply computed by merely counting the number of "1's" in those directions respectively. That is, in step 123, this ellipse $F_o$ is used as the initial image of the shape F which is to be corrected by relaxative approximation. Then, in step 124, the number of "1's" in the direction $Z_i$ of the shape F is counted to compute the thickness $P_i(x, y)$. Then, in step 125, the correction factors $\epsilon_{i1}$ and $\epsilon_{i2}$ are computed according to the equations (12), (13) and (14). In this case, the length $l_i(x, y)$ measured, when the input switch a is connected at its i-side, is used as the true-length projection data. Then, in step 126, the values of $\epsilon_{i1}$ and $\epsilon_{i2}$ obtained in the step 125 are used to correct the shape F thereby obtaining the corrected shape $\overline{F}$. This correction is done by displacing "1" at the boundary between "1's" and "0's" of the shape F toward the direction $Z_i$ (that is, by adding or deducting the number of "1's"). After determination of the corrected shape $\overline{F}$, the number of "1's" in the direction $Z_j$ of $\overline{F}$ is counted in step 127 to compute the thickness $\overline{P_j}$ in the direction $Z_j$. Then, in step 128, the error $\overline{E}$ after correction and the error E before correction are computed according to the equations (15) and (16) respectively. In this case, the input switch b is connected at its j-side, and the length $l_j(x, y)$ is used as the true-length projection data.

Then, in step 129, $|\overline{E}-E|$ is computed to find whether or not the relation (17) is satisfied. When the relation (17) is satisfied, processing is ceased, and, in step 130, the corrected shape $\overline{F}$ is employed as the final shape of F at the specific value of y. On the other hand, when the relation (17) is not satisfied, the shape $\overline{F}$ is deemed as the shape F which is to be corrected. Then, in step 131, the switches a and b are changed over to be connected at the j-side and i-side respectively. Then, the steps of processing described above are repeated until finally the judgment made in step 129 proves that the relation (17) is satisfied, and the final image F (y) is obtained in the step 130. By executing the above processing for each value of y, the three-dimensional shape of the interested part of the object can be determined.

We claim:

1. A method of reconstructing the shape of an interested part of an object through irradiation thereof with X-rays and on the basis of data representative of a distribution of absorbances of the X-rays in the object and displaying the reconstructed shape, comprising:
    a first step of injecting a contrast medium into the object;
    a second step of irradiating the object with first cone-beam like X-rays from a first direction in a first period before the contrast medium reaches the interested part of the object, detecting the X-rays transmitted through the object and producing a first group of data values indicative of absorbances through the object for respective X-ray beams in said first cone-beam like X-rays in said first direction;
    a third step of irradiating the object with second cone-beam like X-rays from said first direction in a second period after the contrast medium reaches the interested part of the object, detecting the X-rays transmitted through the object and producing a second group of data values indicative of absorbances through the object for respective X-ray beams in said second cone-beam like X-rays in said first direction;
    a fourth step of irradiating the object with third cone-beam like X-rays from a second direction transverse from said first direction in a third period before the contrast medium reaches the interested part of the object, detecting the X-rays transmitted through the object and producing a third group of data values indicative of absorbances through the object for respective X-ray beams in said third cone-beam like X-rays in said second direction;
    a fifth step of irradiating the object with fourth cone-beam like X-rays from said second direction in a fourth period after the contrast medium reaches the interested part of the object, detecting the X-rays transmitted through the object and producing a fourth group of data values indicative of absorbances through the object for respective X-ray beams in said fourth cone-beam like X-rays in said second direction;
    a sixth step of subtracting said first data group from said second data group to produce a first projection data image of a distribution of the contrast medium in said interested part in said first direction;
    a seventh step of subtracting said third data group from said fourth data group to produce a second projection data image of a distribution of the contrast medium in said interested part in said second direction;
    an eight step of processing said first and second projection data images to reconstruct a shape of said interested part, said eight step including determining respective widths of projection of said first and second projection data images to establish an ellipse defined by said projection widths as a preliminary shape of said interested part and correcting the shape of said ellipse in accordance with individual data values of said first and second projection data images to provide a corrected shape of said interested part; and
    a ninth step of displaying the corrected shape of said interested part.

2. A method according to claim 1, wherein when said interested part of said object repeats a motion at a substantially constant period, said method further comprises a tenth step of deriving from said object a monitor signal which resembles the motion of said interested part, said first to fourth data groups at said second to fifth steps being taken at the substantially indentical time phases of said monitor signal.

3. A method according to claim 1, wherein the correction at said eight step includes:
    a first phase of detecting the maximum value of said first projection data image and dividing this maximum value by said projection width of said second projection data image to determine an X-ray absorption coefficient of the contrast medium for said first direction;
    a second phase of dividing the individual data values of said first projection data image by the contrast medium absorption coefficient for said first direction to provide thickness values of said interested part in said first direction;
    a third phase of detecting the maximum value of said second projection data image and dividing this maximum value by said projection width of said first projection data image to determine an X-ray absorption coefficient of the contrast medium for said second direction;
    a fourth phase of dividing the individual data values of said second projection data image by the contrast medium absorption coefficient for said second direction to provide thickness values of said interested part in said second direction;

a fifth phase of taking differences between thickness values of said ellipse in one of said first and second directions and the thickness values of said interested part in said one direction to correct the individual thickness values of said ellipse in said one direction in accordance with the results of the differences, thereby producing a corrected shape; and a sixth phase of taking differences between thickness values of said corrected shape in the other of said first and second directions and the thickness values of said interested part in said other direction to judge whether or not the result of the differences satisfies a predetermined relation, wherein when said predetermined relation is satisfied at said sixth phase, said corrected shape produced at said fifth phase is deemed as a final corrected shape of said interested part, and wherein when said predetermined relation is not satisfied at said sixth phase, said fifth and sixth phases are repeated, until said predetermined relation is satisfied, so that the fifth phase is carried out again in conjunction with one of said first and second directions other than the direction taken at the preceding fifth phase while taking the corrected shape produced at that preceding fifth phase as a shape to be newly corrected and the sixth phase is carried out again in conjunction with one of said first and second directions other than the direction taken at the preceding sixth phase and for a corrected shape produced at the again carried-out fifth phase.

4. A method according to claim 1, wherein the injection of the contrast medium at said first step includes first and second injections of the contrast medium, said second and third steps being both carried out in conjunction with the first contrast medium injection, and thereafter said fourth and fifth steps being both carried out in conjunction with the second contrast medium injection.

5. A method according to claim 1, wherein the contrast medium is injected once at said first step, said second and fourth steps being successively carried out before said contrast medium reaches said interested part of said object, and thereafter said third and fifth steps being successively carried out after said contrast medium reaches said interested part of said object.

6. An apparatus for reconstructing the shape of an interested part of an object through irradiation thereof with X-rays and on the basis of data representative of a distribution of absorbances of the X-rays in the object and displaying the reconstructed shape, comprising:

a set of X-ray generating means and X-ray detecting means disposed opposite to each other with the object interposed therebetween so that said X-ray generating means generates cone-beam like X-rays in a predetermined period from each of first and second transverse directions and said X-ray detecting means detects an intensity of the X-rays transmitted through said object;

injector means for injecting a contrast medium into said object;

control circuit means for controlling said X-ray generating means and said injector means, said control circuit means supplying to said injector means a control signal indicative of the injection of the contrast medium into said object, said control circuit means also supplying, to said X-ray generating means, control signals which cause said X-ray generating means to generate first and second cone-beam like X-rays in said first direction in first and second periods before and after the contrast medium reaches the interested part of said object respectively as well as control signals which cause said X-ray generating means to generate third and fourth cone-beam like X-rays in said second direction in third and fourth periods before and after the contrast medium reaches the interested part of said object respectively;

transformation means connected with an output of said X-ray detecting means for transforming output signals of said X-ray detecting means representative of respective intensities of said first to fourth cone beam like X-rays transmitted through said object into absorbance values to produce first to fourth data groups for said first to fourth cone beam like X-rays, each of said first to fourth data groups including data values indicative of absorbances through said object for respective X-ray beams in the corresponding cone-beam like X-rays;

an operation processing section connected with an output of said transformation means, said operation processing means including first operation means for subtracting said first data group from said second data group to produce a first projection data image of a distribution of the contrast medium in said interested part in said first direction while subtracting said third data group from said fourth data group to produce a second projection data image of a distribution of the contrast medium in said interested part in said second direction, second operation means for determining respective widths of projection of said first and second projection data images to generate an ellipse defined by said projection widths as a preliminary shape of said interested part, and third operation means for comparing the shape of said ellipse with individual data values of said first and second projection data images to correct the shape of said ellipse in accordance with those data values into a corrected shape; and display means for displaying the corrected shape produced by said third operation means.

7. An apparatus according to claim 6, wherein said set of X-ray generating means and X-ray detecting means include a pair of X-ray source and X-ray detector arranged opposite to each other on a supporting member which is rotatable to place said pair of X-ray source and X-ray detector into a first fixed position at which they oppose to each other in said first direction and a second fixed position at which they oppose to each other in said second direction, said X-ray source generating said first and second cone-beam like X-rays at said first fixed position and said third and fourth cone-beam like X-rays at said second fixed position, and a time sequence of said first to fourth periods being established in this order.

8. An apparatus according to claim 6, wherein said set of X-ray generating means and X-ray detecting means include a first pair of X-ray source and X-ray detector arranged on a supporting member opposite to each other in said first direction and a second pair of X-ray source and X-ray detector arranged on said supporting member opposite to each other in said second direction, the X-ray source in said first pair generating said first and second cone-beam like X-rays while the X-ray source in said second pair generating said third and fourth cone-beam like X-rays, and a time sequence of said first to fourth periods being established in the order of said first, third, second and fourth periods.

* * * * *